United States Patent [19]
King

[11] Patent Number: 5,156,155
[45] Date of Patent: Oct. 20, 1992

[54] TRANSESOPHAGEAL PROBE SHAFT

[75] Inventor: Robert W. King, Lexington, Mass.

[73] Assignee: Hewlett-Packard Company, Palo Alto, Calif.

[21] Appl. No.: 558,972

[22] Filed: Jul. 25, 1990

[51] Int. Cl.⁵ .............................................. A61B 8/12
[52] U.S. Cl. ............................. 128/662.06; 174/107
[58] Field of Search ...................... 128/662.06, 4–11, 128/675, 419 P

[56] References Cited

U.S. PATENT DOCUMENTS

| | | | |
|---|---|---|---|
| Re. 27,569 | 2/1973 | Ackerman | 128/419 P X |
| 3,244,174 | 4/1966 | Wesbey et al. | 128/419 P |
| 3,568,660 | 3/1971 | King | 128/419 P X |
| 4,590,950 | 5/1986 | Iwaszkiewicz et al. | 128/419 P X |
| 4,667,686 | 5/1987 | Peers-Travarton | 128/419 P X |
| 4,679,572 | 7/1987 | Baker, Jr. | 128/419 P X |
| 4,729,284 | 3/1988 | Bazenet . | |
| 4,730,389 | 3/1988 | Baudino et al. | 128/419 P X |
| 4,928,699 | 5/1990 | Sasai | 128/662.06 |
| 4,951,677 | 8/1990 | Crowley et al. | 128/662.06 |
| 4,991,588 | 2/1991 | Pflueger et al. | 128/662.06 |
| 5,050,539 | 6/1991 | Yokoi et al. | 128/662.06 |

FOREIGN PATENT DOCUMENTS

| | | |
|---|---|---|
| 0062315 | 10/1982 | European Pat. Off. . |
| 0234951 | 9/1987 | European Pat. Off. . |
| 2584288 | 1/1987 | France . |

*Primary Examiner*—Francis Jaworski

[57] ABSTRACT

A shaft for an invasive probe used for medical applications which includes a central core, a metal sheath surrounding the core and an outer elastomeric coating. A dielectric sleeve is disposed between the core and sheath for electrically isolating the core from the sheath. A dielectric spacer used in conjunction with a fitting disposed at the end of the shaft completely seals the core from other portions of the probe to protect the patient from electrical currents carried by wires within the core. The wires are also protected from damage from bodily fluids and cleaning solutions by the dielectric sleeve and spacer, since the core is sealed from the environment.

18 Claims, 1 Drawing Sheet

TRANSESOPHAGEAL PROBE SHAFT

FIELD OF THE INVENTION

This invention relates generally to probes for use with body cavities, and more particularly to a transesophageal probe.

BACKGROUND OF THE INVENTION

Ultrasonic transducers, and in particular, phased array ultrasonic transducers, are frequently utilized for a variety of medical applications. In one such application, the transducer is disposed at the end of an endoscope which is suitably positioned in the patient's esophagus for scanning such internal organs as the heart. When used in this manner, this transducer or probe is referred to as a transesophageal probe, and the procedure is referred to as transesophageal echocardiography (TEE) when the probe is utilized for scanning the heart. Other invasive probes which have similar structures and requirements include transrectal, transnasal and transvaginal probes.

The shaft of the endoscope serves as an enclosure for electrical and mechanical cables which couple the transducer and other electrical components of the endoscope to an external power source and external controls. Since a probe of this type and its shaft is positioned inside the body, the probe and shaft must be sealed to protect them against attack from body fluids and acids, as well as against sterilizing solutions and cleaning solutions either inside or outside the body. Moreover, the probe and shaft must protect the patient from currents carried by the electrical cables. Thus, the transducer, as well as the shaft of the endoscope must be enclosed within an insulative protective outer covering. Such a covering also protects the body from irritation as result of probe rotation.

Existing shafts of such transesophageal probes typically comprise an inner, convoluted metal core which provides the required crush resistance to the shaft, a stainless steel braided sheath which is constructed over this inner core, and an outer coating of an elastomeric material. The elastomeric material serves as an insulator to protect the patient from electric currents, as a smooth, corrosion resistant surface to facilitate the placement of the probe and as a cover to protect the mechanical and electrical components of the endoscope from damage by bodily fluids.

One of the major causes of failure of this type of probe shaft is the physical penetration of this outer elastomeric coating by the patient, for example as a result of the teeth of the patient being clamped tightly about the shaft or as a result of the shaft being rubbed against the patient's teeth during insertion of the probe. Even with the most cut-through resistant, flexible coatings available, such as urethanes, eventually the coating is penetrated by the patient's teeth, or by wear and tear from other sources. These penetrations are exacerbated by exposure to stomach acid, cold sterilants and cleaning fluids commonly used in a clinical setting. Once the elastomeric coating is penetrated, there is a direct, electrically conductive path between the patient and the probe, thereby introducing a potential safety risk to the patient. Even a single small penetration of the outer elastomeric coating can provide a direct electrical path to the patient, once the probe has been inserted into the esophagus.

It is therefore an object of the present invention to provide a shaft for an invasive body probe which is resistant to penetration therethrough to the interior core during normal use.

It is another object of the present invention to provide a shaft for an invasive body probe which electrically insulates the patient from the conductive metal portion of the shaft, even if the outer coating is penetrated.

It is another further object of the present invention to provide a shaft for an invasive body probe which adequately protects the shaft from damage caused by the patient during normal use.

It is yet another further object of the present invention to provide a flexible, hollow shaft for use in a transesophageal probe which provides an enclosure for electrical and mechanical cables, and which adequately protects the cables and the patient from damage resulting by penetration of the shaft coating by the patient during use.

SUMMARY OF THE INVENTION

The foregoing and other objects are achieved in accordance with the present invention which relates to a shaft for an invasive body probe, particularly a transesophageal probe, which protects the probe from damage and avoids any risk of injury to the patient even if the outer coating is penetrated by the patient during use. The shaft of the present invention includes a crush proof core, a stainless steel braided sheath and a dielectric, flexible sleeve sandwiched between the sheath and the core. The entire structure is coated with a tough elastomeric material. A fitting is adhered to each end of this structure, and is bonded to the stainless steel braid. A dielectric spacer is disposed between a fitting attached to adjacent components and the fitting bonded to the braid. An end of the dielectric sleeve is sandwiched between the dielectric spacer and the fitting attached to the sheath to electrically isolate the core and the interior cables within the core from the rest of the probe.

The dielectric sleeve is protected from any danger of cutthrough by the stainless steel sheath, and the stainless steel sheath is electrically insulated from the core. Thus, even if the outer elastomeric coating is penetrated, the patient will not be subject to any danger. Furthermore, the electrical and mechanical cables and components of the shaft and probe are protected from damage during normal use.

BRIEF DESCRIPTION OF THE DRAWINGS

The objects, advantages and features of this invention will be more clearly appreciated from the following detailed description when taken in conjunction with the accompanying drawings in which.

DETAILED DESCRIPTION OF THE PREFERRED EMBODIMENTS

Figure 1:
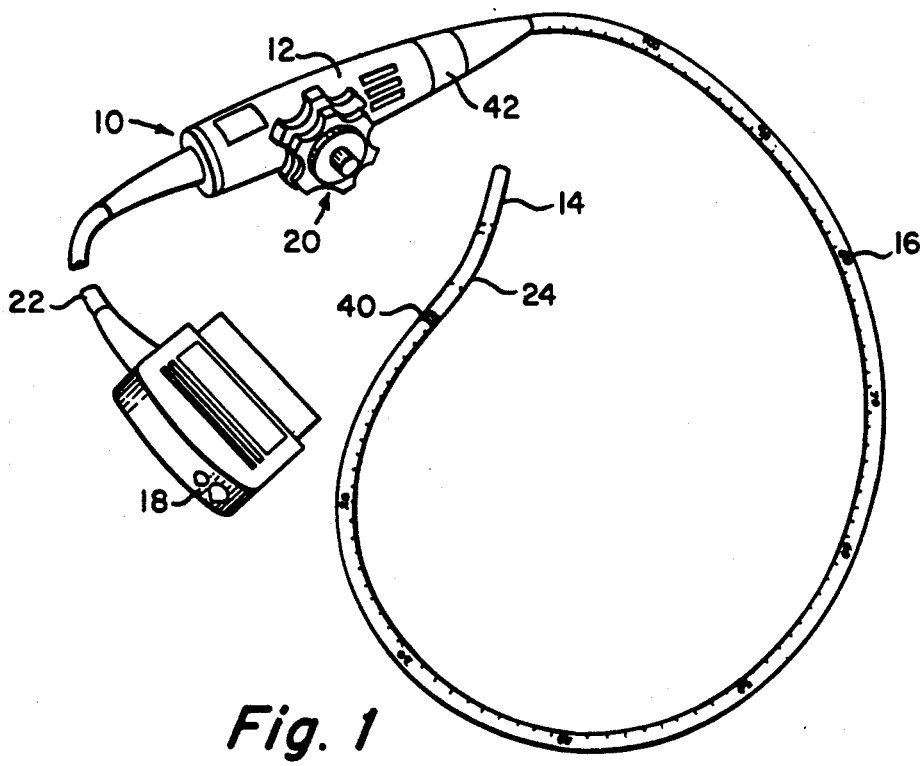
FIG. 1 is a pictorial representation of a transesophageal probe utilizing the shaft of the present invention.

With reference now to the drawings, and more particularly to FIG. 1 thereof, there is shown a pictorial representation of a typical transesophageal probe 10 with which the shaft of the present invention is used. It is to be understood that this invention is being described with reference to a transesophageal probe for purposes of illustration only, and that this invention has equal applicability to other invasive body probes which utilize a shaft which must be protected from damage, and which must be electrically insulated from the patient, such as transrectal, transnasal and transvaginal probes.

Probe 10 includes a proximal head portion 12, a distal tip portion 14, a somewhat flexible shaft 16 connecting head portion 12 with distal tip portion 14 and electrical connector 18. Shaft 16 may include a flexible portion 24 adjacent distal tip portion 14 which can be bent. Distal tip portion 14 typically includes a transducer (not shown), and electrical cables 22 travel from connector 18, through head portion 12 and shaft 16 to the transducer. Typically, distal tip portion 14 can be deflected for proper positioning of the transducer by bending of portion 24. This deflection is produced by rotation of wheels 20 which are mechanically coupled to portion 24 by cables and the like (not shown) which travel through shaft 16. The manner of operation of transesophageal probe 10, and the details of its structure are well known to those skilled in the art, and need not be further discussed herein.

Figure 2:
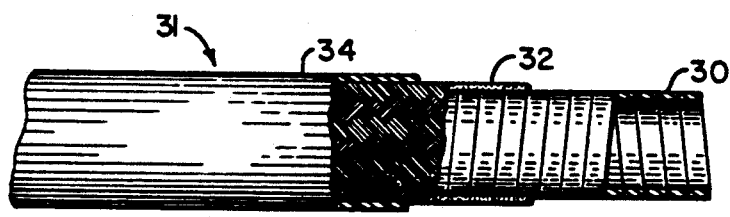
FIG. 2 is a partially cutaway cross sectional side view of a section of a prior art shaft.

A typical prior art shaft 31 is shown in FIG. 2. The prior art shaft of FIG. 2 comprises three components: an inner convoluted core 30, a stainless steel braided sheath 32 and an outer, elastomeric coating 34. As can be seen, sheath 32 is electrically coupled to core 30. Core 30 provides crush resistance to the shaft, and sheath 32 provides torsional stiffness. The stainless steel sheath is typically constructed over the inner core by feeding the core through a standard braiding machine. Outer elastomeric coating 34 typically comprises an extruded tube stretched over stainless steel sheath 32. In an alternative configuration, coating 34 may be dipped or brushed onto sheath 32. Elastomeric coating 34 both protects sheath 32 and provides a smooth, soft surface to the patient to prevent injury when inserting distal tip portion 14. Also, an elastomeric material can be easily sterilized, since it presents a smooth outer surface lacking any crevices in which bacteria can hide.

During use of the transesophageal probe 10, distal tip portion 14 is inserted into the patient's mouth and down his esophagus to be positioned therein for scanning of the heart, or other bodily organs. During this process, some abrasion of the outer surface of shaft 16 can occur, and the patient could inadvertently bite down on shaft 16 during the process. Should a patient puncture coating 34 of shaft 31, he could become electrically connected to the electrical cables passing from connector 18 to distal tip 14. Furthermore, gastric juices and the like could penetrate braid 32, and enter the interior of core 30, thus possibly damaging the mechanical and electrical cables and other components passing therethrough.

Figure 3:
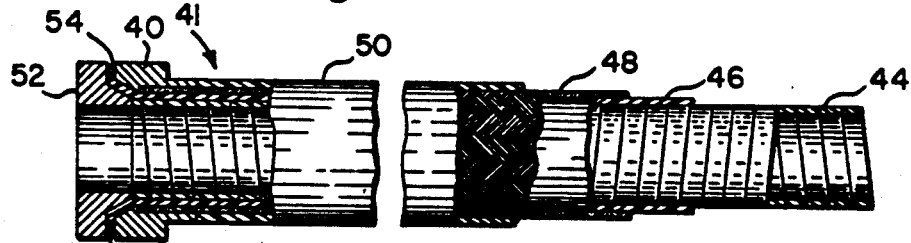
FIG. 3 is a partially cutaway cross sectional side view showing the probe shaft of the present invention.

Shaft 41 of the present invention, which comprises at least a portion of shaft 16, will now be described with particular reference to FIGS. 1 and 3. Shaft 41 extends between fittings 40 and 42, which assist in securing shaft 41 to adjacent sections of probe 10. Fitting 40 typically is disposed immediately adjacent portion 24, while fitting 42 typically is disposed in head portion 12, although either fitting may be disposed at other positions along shaft 16, the actual locations depending on the length of portion of shaft 16 for which it is desired that the core be electrically insulated from the patient. Fittings 40 and 42 are identical, and only fitting 40 is shown in FIG. 3 for illustration. Shaft 41 includes an inner convoluted core 44, a stainless steel sheath 48 surrounding core 44, a flexible sleeve 46 disposed between sheath 48 and core 44, and an outer, tough, elastomeric coating 50 covering sheath 48. Core 44, sheath 48 and coating 50 may be similar to core 30, sheath 32 and coating 34 respectively of shaft 31. Core 44 typically is composed of stainless steel, while sheath 48 typically is formed of braided stainless steel. Coating 50 typically is dipped or brushed onto sheath 48, or in an alternative embodiment, it may comprise an extruded tube which has been stretched over sheath 48.

Sleeve 46 is formed of a dielectric material which electrically insulates sheath 48 from core 44. An example is an elastomeric material such as polyvinylchloride. Sleeve 46 includes end portions 54, each of which extends beyond an end of sheath 48 at opposite ends of shaft 41 adjacent fittings 40 and 42, as will be described. Portions 54 of sleeve 46 are caused to extend beyond adjacent ends of sheath 48 by peeling back sheath 48 at each end. Each of fittings 40 and 42 is bonded to an end of sheath 48, such as by gluing, brazing or the like.

Figure 4:
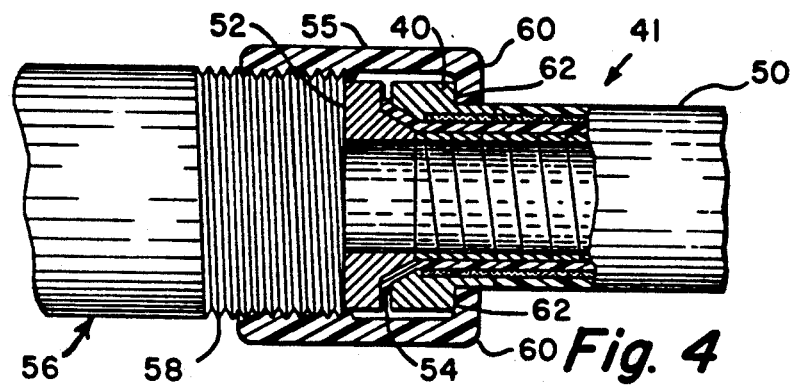
FIG. 4 is a partially cutaway cross sectional side view showing the coupling mechanism associated with the probe shaft of FIG. 3.

A preferred manner of attachment of shaft 41 to adjacent sections of probe 10, such as portion 24 or head portion 12 is shown in FIG. 4. Since shaft 41 is secured at either end in an identical manner, only the attachment of shaft 41 at one end by the use of fitting 40 will be described herein. During assembly, an annular spacer 52 is inserted into each end of shaft 41 to capture portion 54 of sleeve 46 between spacer 52 and respective fitting 40 or 42. The adjacent section of probe 10 to which shaft 41 is secured, such as portion 24 or head portion 12, includes an attached fitting 56 having an enlarged, threaded portion 58 disposed at an end thereof facing fitting 40 or 42. A nut 55 is loosely positioned over fitting 40 or 42 and includes inner threads adapted to cooperatively mate with threads on the exterior surface of enlarged portion 58. As portion 58 is brought into contact with spacer 52, nut 55 is rotated to permit its threads to engage those threads of portion 58, thereby drawing portion 58 towards spacer 52. Nut 55 includes a radially inwardly extending surface 60 which is adapted to engage shoulder 62 of fitting 40 to limit the advance of nut 55 axially along shaft 41 toward fitting 56. As nut 55 is tightened, fitting 56 is drawn towards spacer 52 and fitting 40 to tightly compress portion 58 against spacer 52. As a result, portion 54 is tightly captured between fitting 40 and spacer 52.

Typically, prior to threading nut 55 onto portion 58, the threads of nut 55 are coated with a thermosetting resin, such as epoxy, so that after nut 55 is tightened, the epoxy cures and the threaded connection between nut 55 and portion 58 is permanently sealed against fluid penetration. Preferably, nut 55 is formed of a dielectric material, such as a fiberglass (glass/epoxy). Spacer 52 is formed of a dielectric material, preferably a plastic such as a phenolic.

Sleeve 46 seals and insulates the inner surface of core 44 from sheath 48. Sleeve 46, spacers 52, portions 54 and nuts 55 all cooperate to insulate the inner surface of core 44 from other portions of probe 10 along the entire length of core 44. Also spacers 52, portions 54 and nuts 55 electrically insulate fittings 56 from fittings 40 and 42, and thus, shaft 41. Therefore, core 44 is not in electrical contact with sheath 48, or with any other portion of the assembly at any point. Should coating 50 be penetrated, the patient cannot come into electrical contact with core 44, since sheath 48 is now electrically insulated from core 44. Sleeve 46 is protected by sheath 48 from penetration by the patient, so that even if the patient penetrates coating 50, he cannot penetrate sleeve 46. Finally, should gastric juices or the like penetrate sheath 48, they are prevented by sleeve 46 from reaching core 44 or the electrical or mechanical components contained within core 44.

It is to be understood that core 44 may be composed of other materials besides stainless steel, so long as the required strength, rigidity and structural support are provided to prevent crushing of the core. Similarly, while a stainless steel braid is preferred for sheath 48, another similarly corrosion resistant, strong, durable material could be used. Also, while an elastomeric material is preferred for sleeve 46 and coating 50, other equally durable, corrosion resistant, dielectric materials could be utilized. Furthermore, other mechanisms may be used for coupling shaft 41 to adjacent sections of probe 10. The use of a threaded nut is intended to be exemplary only. Shaft 41 may also be coupled to adjacent sections of probe 10 by a clamping mechanism or by any other suitable device which would join fitting 56 to shaft 41 and capture spacer 52 therebetween to electrically insulate shaft 41 from the rest of probe 10.

In a preferred embodiment, shaft 41 of this invention is prepared by first forming core 44 by wrapping a strip of stainless steel or the like about a mandril, as is well known in the art. Typically, a piece of dielectric, previously formed tubing is slid over core 44 after formation of core 44 to comprise sleeve 46. Sheath 48 is constructed over sleeve 46 by feeding sleeve 46 and core 44 through a standard braiding machine. Thereafter, elastomeric coating 50 is painted on, or is preformed and slid onto sheath 48. At each end of shaft 16, sheath 48 is peeled back to expose end portion 54 of sleeve 46. Fittings 40 and 42 are then bonded to opposite ends of sheath 48, such as by gluing, brazing or the like. A spacer 52 is inserted at each end of shaft 41 at fittings 40 and 42 and is held in place by compressing it between a fitting 56 and fitting 40 or 42, such as by a nut 55, as described, which couples shaft 41 to adjacent sections of probe 10.

In view of the above description, it is likely that modifications and improvements will occur to those skilled in the art which are within the scope of this invention. The above description is intended to be exemplary only, the scope of the invention being defined by the following claims and their equivalents.

What is claimed:

1. A shaft for use with a probe adapted to invade a bodily cavity, said shaft comprising:
   an inner, electrically conductive core having a length and defining a channel extending along the length of the shaft;
   means sealing said core for electrically and chemically isolating said core from any environment outside of said shaft, said isolating means comprising a dielectric sleeve encircling said core and extending at least along a substantial portion of the length of said core and a pair of dielectric plugs contacting respective opposite ends of said sleeve;
   a flexible sheath surrounding the exterior of said sleeve, said sheath having a length, said sheath being electrically insulated from said core along the length of said sheath by said sleeve; and
   an outer electrically insulative coating covering said sheath.

2. A shaft as recited in claim 1 wherein said sleeve is composed of an elastomeric material.

3. A shaft as recited in claim 1 further comprising a plurality of fittings, each disposed at a respective end of said shaft and each adapted to couple said shaft to at least one other component of the probe.

4. A shaft as recited in claim 3 wherein each of said fittings is bonded to said sheath.

5. A shaft for use with a probe adapted to invade a bodily cavity, said shaft comprising:
   an inner, electrically conductive core having a length and defining a channel extending along the length of the shaft;
   a dielectric sleeve encircling said core and extending at least along a substantial portion of the length of said core;
   a flexible sheath surrounding the exterior of said sleeve and capturing said sleeve between said sheath and said core, said sheath having a length, said sheath being electrically insulated from said core along the length of said sheath by said sleeve;
   an outer, electrically insulative coating covering said sheath;
   a fitting disposed at each end of said shaft and adapted to couple said shaft to other components of the probe; and
   at each end of said shaft;
      a portion of said sleeve extending beyond said core and beyond an end of said sheath; and
      a dielectric spacer disposed adjacent a surface of said fitting, said portion of said sleeve being captured between said spacer and said surface of said fitting.

6. A shaft as recited in claim 5 further comprising means disposed at each end of said shaft for coupling said fitting to other components of said probe and for capturing said spacer between said coupling means and said fitting.

7. A shaft as recited in claim 6 wherein one of said coupling means disposed at one end of said shaft couples said one end of said shaft to a distal tip containing a transducer, and wherein another of said coupling means disposed at an opposite end of said shaft couples said opposite end of said shaft to a head portion of the probe.

8. A shaft as recited in claim 7 wherein said core is electrically insulated from said distal tip and from said head portion of the probe.

9. A transesophageal probe comprising:
   a distal tip portion containing a transducer;
   a head portion containing means for adjusting the position of said distal tip portion; and
   a shaft coupling said head portion to said distal tip portion and having a central channel containing electrical and mechanical connections extending from said head portion to said distal tip portion, said shaft comprising:
      a central core enclosing said channel, said core having a length, said core being sufficiently flexible to permit bending of said shaft, but being sufficiently rigid to prevent collapse of said channel;

an electrically insulating sleeve encircling said core and extending at least along a substantial portion of the length of said core;

a flexible sheath surrounding said sleeve, said sheath being formed of a material sufficiently strong to resist puncturing, said sheath being electrically insulated from said core by said sleeve;

an electrically insulating, corrosion resistant, flexible material covering said sheath on an exterior surface thereof;

a first fitting disposed at an end of said shaft adjacent said distal tip portion;

a second fitting disposed at an end of said shaft adjacent said head portion;

an end portion of said sleeve disposed at each end of said shaft extending beyond said sheath;

a first dielectric spacer disposed adjacent said first fitting, an end portion of said sleeve being disposed between said first fitting and said first spacer;

a second dielectric spacer disposed adjacent said second fitting, an end portion of said sleeve being disposed between said second fitting and said second spacer;

first means for coupling said first fitting to said distal tip portion to capture the end portion of said sleeve between said first fitting and said first spacer; and second means for coupling said second fitting to said head portion to capture the end portion of said sleeve between said second fitting and said second spacer.

10. A transesophageal probe as recited in claim 9 wherein said first and said second fittings are both bonded to said sheath.

11. A shaft for use with a probe adapted to invade a bodily cavity, said shaft comprising:

an inner, electrically conductive core having a length and defining a channel extending along the length of the shaft;

means sealing said core for electrically and chemically isolating said core from any environment outside of said shaft, said isolating means comprising:

a dielectric sleeve encircling said core and extending at least along a substantial portion of the length of said core;

a fitting disposed at one end of said shaft and adapted to couple said shaft to at least one other component of the probe; and a dielectric spacer disposed at the one end of said shaft and adjacent a surface of said fitting;

a flexible sheath surrounding the exterior of said sleeve, said sheath having a length, said sheath being electrically insulated from said core along the length of said sheath by said sleeve; and an outer, electrically insulative coating covering said sheath;

wherein a portion of said sleeve, extending beyond said core and beyond an end of said sheath proximal the one end of said shaft, is captured between said spacer and said surface of said fitting.

12. A shaft as recited in claim 11 wherein said isolating means further comprises means disposed at the one end of said shaft for coupling said fitting to the at least one other component of the probe and for capturing said spacer between said coupling means and said fitting.

13. A shaft for use with a probe adapted to invade a bodily cavity, said shaft comprising:

an inner, electrically conductive core having a length and defining a channel extending along the length of the shaft;

a dielectric sleeve encircling said core and extending at least along a substantial portion of the length of said core;

a flexible sheath surrounding the exterior of said sleeve, said sheath having a length, said sheath being electrically insulated from said core along the length of said sheath by said sleeve;

an outer, electrically insulative coating covering said sheath;

a fitting disposed at one end of said shaft and adapted to couple said shaft to at least one other component of the probe; and a dielectric spacer disposed adjacent a surface of said fitting, wherein a portion of said sleeve, extending beyond an end of said sheath proximal the one end of said shaft, is captured between said spacer and said surface of said fitting.

14. A shaft as recited in claim 13 further comprising means disposed at the one end of said shaft for coupling said fitting to the at least one other component of said probe and for capturing said spacer between said coupling means and said fitting.

15. A shaft as recited in claim 13 wherein:

said shaft further comprises a distal tip portion containing a transducer;

said shaft further comprises a head portion containing means for adjusting the position of said distal tip portion; and said core couples said head portion to said distal tip portion and encloses said channel;

said channel comprises a central channel containing electrical and mechanical connections extending from said head portion to said distal tip portion;

said core is sufficiently flexible to permit bending of said shaft, but is sufficiently rigid to prevent collapse of said channel;

said sleeve comprises an electrically insulating and chemically resistant sleeve;

said sheath is formed of a material sufficiently strong to resist puncturing; and said coating comprises an electrically insulating, corrosion resistant, flexible material covering said sheath on an exterior surface thereof.

16. A shaft as recited in claim 13 wherein said fitting is bonded to said sheath.

17. A shaft as recited in claim 13 wherein said sleeve is formed of an elastomeric material.

18. A shaft as recited in claim 13 wherein said sheath is formed of braided stainless steel.

* * * * *